United States Patent
Song et al.

(10) Patent No.: US 8,134,042 B2
(45) Date of Patent: Mar. 13, 2012

(54) WETNESS SENSORS

(75) Inventors: Xuedong Song, Roswell, GA (US);
Darold D. Tippey, Brunswick, GA (US);
Jessica Sara Van Handel, Menasha, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 839 days.

(21) Appl. No.: 11/956,657

(22) Filed: Dec. 14, 2007

(65) Prior Publication Data
US 2009/0157025 A1    Jun. 18, 2009

(51) Int. Cl.
*A61F 13/15*    (2006.01)
(52) U.S. Cl. ........................................ 604/361
(58) Field of Classification Search .................... 604/361
See application file for complete search history.

(56) References Cited

U.S. PATENT DOCUMENTS

| | | | |
|---|---|---|---|
| 4,032,661 A | 6/1977 | Rowsell et al. |
| 4,121,011 A | 10/1978 | Glover et al. |
| 4,136,163 A | 1/1979 | Watson et al. |
| 4,192,311 A | 3/1980 | Felfoldi |
| 4,230,688 A | 10/1980 | Rowsell et al. |
| 4,231,370 A | 11/1980 | Mroz et al. |
| 4,459,425 A | 7/1984 | Amano et al. |
| 4,507,121 A | 3/1985 | Leung |
| 4,642,250 A | 2/1987 | Spector |
| 4,653,491 A | 3/1987 | Okada et al. |
| 4,681,576 A | 7/1987 | Colon et al. |
| 4,704,116 A | 11/1987 | Enloe |
| 4,705,513 A | 11/1987 | Sheldon et al. |
| 4,725,462 A | 2/1988 | Kimura |
| 4,826,550 A | 5/1989 | Shimizu et al. |
| 5,003,178 A | 3/1991 | Livesay |
| 5,192,606 A | 3/1993 | Proxmire et al. |
| 5,197,958 A | 3/1993 | Howell |
| 5,221,228 A | 6/1993 | Pedroia |
| 5,266,592 A | 11/1993 | Grub et al. |
| 5,389,093 A | 2/1995 | Howell |
| 5,399,219 A | 3/1995 | Roessler et al. |
| 5,486,166 A | 1/1996 | Bishop et al. |
| 5,490,846 A | 2/1996 | Ellis et al. |
| 5,540,796 A | 7/1996 | Fries |
| 5,595,618 A | 1/1997 | Fries |
| 5,702,377 A | 12/1997 | Collier, IV et al. |
| 5,931,823 A | 8/1999 | Stokes et al. |

(Continued)

FOREIGN PATENT DOCUMENTS

EP    1424918    11/2005

(Continued)

OTHER PUBLICATIONS

International Search Report from PCT/IB2008/053676—8 pages.

*Primary Examiner* — Lynne Anderson
(74) *Attorney, Agent, or Firm* — Dority & Manning, P.A.

(57) ABSTRACT

In accordance with one embodiment of the present disclosure a method for detecting the presence of urine is described. The method includes providing a urine indicating sensor with a porous matrix, the matrix having a pH indicator non-diffusively immobilized thereon, the pH indicator being capable of a color transition when in contact with urine. Urine is contacted with the matrix of the sensor and the presence of urine is determined based on whether the pH indicator undergoes a color transition.

17 Claims, 2 Drawing Sheets

U.S. PATENT DOCUMENTS

| | | | |
|---|---|---|---|
| 5,962,995 A | 10/1999 | Avnery | |
| 6,060,638 A | 5/2000 | Paul et al. | |
| 6,150,002 A | 11/2000 | Varona | |
| 6,270,783 B1 | 8/2001 | Slavtcheff et al. | |
| 6,407,492 B1 | 6/2002 | Avnery et al. | |
| 6,486,227 B2 | 11/2002 | Nohr et al. | |
| 6,617,488 B1 * | 9/2003 | Springer et al. | 604/361 |
| 6,627,233 B1 | 9/2003 | Wolf et al. | |
| 6,635,797 B2 | 10/2003 | Olson et al. | |
| 6,642,427 B2 * | 11/2003 | Roe et al. | 604/361 |
| 6,663,611 B2 | 12/2003 | Blaney et al. | |
| 6,733,766 B2 | 5/2004 | Gott et al. | |
| 6,772,708 B2 * | 8/2004 | Klofta et al. | 116/206 |
| 6,780,896 B2 | 8/2004 | MacDonald et al. | |
| 7,002,054 B2 * | 2/2006 | Allen et al. | 604/361 |
| 7,306,764 B2 * | 12/2007 | Mody | 422/58 |
| 2003/0125682 A1 | 7/2003 | Olson et al. | |
| 2003/0164136 A1 | 9/2003 | Klofta et al. | |
| 2004/0102750 A1 | 5/2004 | Jameson | |
| 2005/0054255 A1 | 3/2005 | Morman et al. | |
| 2005/0059941 A1 | 3/2005 | Baldwin et al. | |
| 2005/0137542 A1 * | 6/2005 | Underhill et al. | 604/361 |
| 2006/0229577 A1 * | 10/2006 | Roe et al. | 604/361 |
| 2007/0156106 A1 * | 7/2007 | Klofta et al. | 604/361 |

FOREIGN PATENT DOCUMENTS

| | | |
|---|---|---|
| WO | WO 93/19716 A1 | 10/1993 |
| WO | WO 9516425 | 6/1995 |
| WO | WO 00/00082 A1 | 1/2000 |
| WO | WO 0112150 | 2/2001 |

* cited by examiner

WETNESS SENSORS

BACKGROUND

Disposable absorbent articles such as diapers, training pants, incontinence pads, and the like are highly absorbent and efficiently pull moisture away from the wearer, reducing skin irritation caused by prolonged wetness exposure. However, because these articles are so absorbent, wearers may not realize they have urinated, particularly if they are inexperienced toddlers who may not recognize the meaning of body sensations associated with urination. Thus, the wearer may not recognize their urination control failure or be aware the article should be changed. Furthermore, parents or caregivers may not recognize that the absorbent article requires changing.

Visual mechanisms have also been employed to signal the presence of wetness in absorbent articles. There are a large number of wetness sensing technologies that currently exist including electronic-based wetness sensors, color-based wetness sensors, and enzyme-based wetness sensors. However, such conventional sensors are often complicated and costly. In addition, the signals produced by such sensors are often only present for a short period of time. Additionally, conventional sensing technologies do not provide a back-up to confirm accurate test results.

Thus, a need exists for efficient sensors that do not need careful monitoring to produce accurate urine detection. An absorbent article that incorporates such a sensor would be particularly beneficial.

SUMMARY

In accordance with one embodiment of the present disclosure a method for detecting the presence of urine is described. The method includes providing a urine indicating sensor with a matrix, the matrix having a pH indicator non-diffusively immobilized thereon, the pH indicator being capable of a color transition when in contact with urine. Urine is contacted with the matrix of the sensor and the presence of urine is determined based on whether the pH indicator undergoes a color transition.

In another embodiment of the present disclosure, a method for detecting the presence of urine is described. The method includes providing a urine indicating sensor with a porous matrix, the matrix having a mixture of a thermochromic material and a temperature change agent disposed thereon, the temperature change agent, when brought into contact with urine, being capable of causing a temperature change in the thermochromic material resulting in a color transition. Urine is contacted with the matrix of the sensor and the presence of urine is determined based on whether the thermochromic material undergoes a color transition.

Other features and aspects of the present disclosure are discussed in greater detail below.

BRIEF DESCRIPTION OF THE DRAWINGS

A full and enabling disclosure, including the best mode thereof, directed to one of ordinary skill in the art, is set forth more particularly in the remainder of the specification, which makes reference to the appended figure in which.

Figure 1:
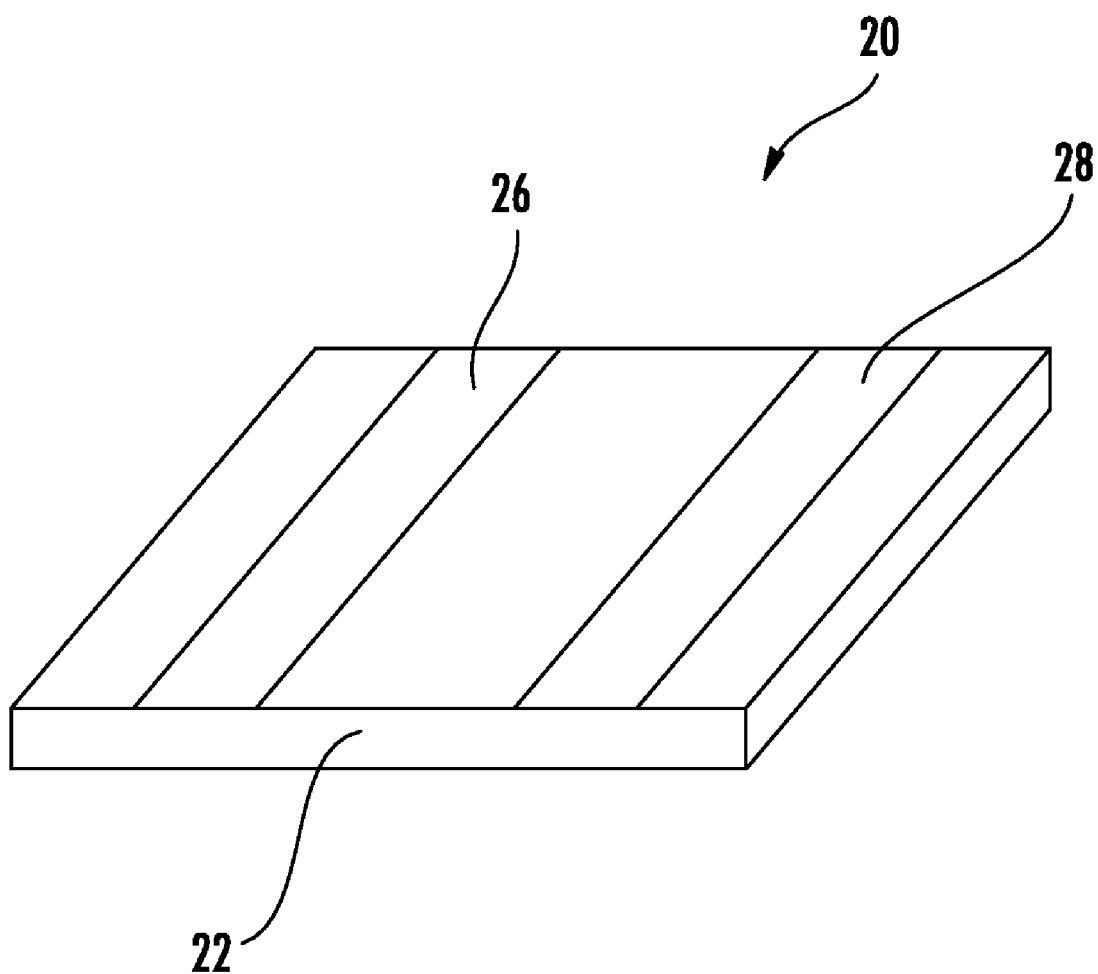
FIG. 1 is a perspective view of one embodiment of a sensor that can be used in the present disclosure.

Repeat use of reference characters in the present specification and drawings is intended to represent same or analogous features or elements of the disclosure.

DETAILED DESCRIPTION

Reference now will be made in detail to various embodiments of the disclosure, one or more examples of which are set forth below. Each example is provided by way of explanation of the disclosure, not limitation of the disclosure. In fact, it will be apparent to those skilled in the art that various modifications and variations can be made in the present disclosure without departing from the scope or spirit of the disclosure. For instance, features illustrated or described as part of one embodiment, can be used on another embodiment to yield a still further embodiment. Thus, it is intended that the present disclosure covers such modifications and variations as come within the scope of the appended claims and their equivalents.

In general, the present disclosure is generally directed to sensors for determining the presence or absence of urine. The sensors can utilize non-diffusively immobilized pH indicators and/or thermochromic mixtures to accurately detect the presence or absence of urine.

Non-diffusive immobilization of a pH indicator on a solid matrix can greatly extend the period of time that the urine detection signal remains stable, even after multiple insults. Similarly, the thermochromic mixtures described herein can produce signals that remain stable for extended periods of time, while also being capable of withstanding multiple insults. Sensors that combine the pH indicator and thermochromic mixtures can provide reliable back-up detection of urine.

The sensors described herein provide a simple, user-friendly, cost-effective approach for rapid determination of wetness caused by urine. Additionally, the sensors described herein can be incorporated into absorbent articles such as diapers and incontinent articles to assist in detecting urine wetness.

Referring to FIG. 1, one embodiment of a sensor 20 that can be formed according to the present disclosure will now be described in more detail. As shown, the sensor 20 includes a matrix 22. In general, the matrix 22 can be made from any of a variety of materials through which the urine is capable of passing. For example, the matrix 22 can be a porous membrane formed from synthetic or naturally occurring materials, such as polysaccharides (e.g., cellulose materials such as paper and cellulose derivatives, such as cellulose acetate and nitrocellulose); polyether sulfone; polyethylene; nylon; polyvinylidene fluoride (PVDF); polyester; polypropylene; silica; inorganic materials, such as deactivated alumina, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon or rayon); porous gels, such as silica gel, agarose, dextran, and gelatin; polymeric films, such as polyacrylamide; and so forth. In one particular embodiment, the matrix 22 is formed from a Biodyne® Plus membrane, a positively charged Nylon membrane, made by Pall Corporation. In another embodiment, the matrix is formed from a porous cellulose based material such as filter paper and tissue that are made positively charged through treatment of positively charged polymers.

The size and shape of the matrix 22 can generally vary as is readily recognized by those skilled in the art. For instance, the matrix can have a length and width of from about 10 to about 100 millimeters, in some embodiments from about 20 to about 80 millimeters, and in some embodiments, from about 40 to about 60 millimeters. The thickness of the matrix can be less than about 500 micrometers, in some embodiments less than about 250 micrometers, and in some embodiments, less than about 150 micrometers.

To initiate detection of the presence or absence of urine, a user can directly apply the test sample to a portion of the matrix 22. In the illustrated embodiment, the matrix 22 defines a pH indicator zone 26 and a thermochromic zone 28. However, it should be understood that in certain embodiments, either the pH indicator zone or the thermochromic zone can be the only zone present on the matrix.

To facilitate detection of urine, a pH indicator is non-diffusively immobilized in the pH indicator zone 26. The pH indicator can be applied directly to the matrix 22 or first formed into a solution prior to application. Various solvents can be utilized to form the solution, such as, but not limited to, acetonitrile, dimethylsulfoxide (DMSO), ethyl alcohol, dimethylformamide (DMF), and other polar organic solvents. The amount of the pH indicator in the solution can range from about 0.001 to about 100 milligrams per milliliter of solvent, and in some embodiments, from about 0.1 to about 10 milligrams per milliliter of solvent. The pH indicator concentration can be selectively controlled to provide the desired level of detection sensitivity.

It is desired that the pH indicator be applied in a manner so that it does not substantially diffuse through the matrix 22 (i.e., non-diffusively immobilized). The pH indicator is configured to have a color transition when exposed to pH levels that are within the range of typical pH for urine (either greater than about 5.5 or less than about 10). The pH indicator produces an initial color based on a pH outside of the range of typical pH for urine (less than about 5.5 or greater than about 10). Once the urine sample contacts the pH indicator, the urine causes a pH change to induce a color change in the pH indicator signaling that urine has contacted the matrix.

The preferred pH indicators and their derivatives have a color transition pH of either greater than about 10 or less than about 5.5. Examples of suitable pH indicators with a color transition at less than about 5.5 include Chlorobromophenol blue, Bromophenol blue, Bromocresol blue, methyl violet, methyl orange, Congo red, leucomalachite green, methyl yellow, bromophenol blue, malachite green, brillian green, crystal violet, erythrosin B, methyl green, methyl violet 2B, picric acid, napthol yellow S, quinaldine red, basic fuchsin. Examples of pH indicators with a color transition of greater than about 10 include nile blue A, thymolphthalein, aniline blue W.S., alizarin yellow GG, morgant orange I, tropaeolin O, orange G, acid fuchsin, thiazol yellow G, indigo carmine, phenolphthalein, thymolphthalein, alizarine yellow R. Derivatives of such pH indicators are also useful for making sensors in accordance with the present disclosure.

However, any suitable pH indicator as would be known in the art is contemplated for use in the present disclosure.

In certain embodiments, the initial color of the immobilized pH indicator can be easily adjusted by immobilizing the indicator along with a pH adjuster, either an acid, a buffer, a base or some combination thereof. The initial color is important to provide a sharp color contrast as large as possible. For instance, when bromothymol blue is used as an indicator, basic condition gives the indicator zone a vivid green color, which is clearly distinguishable from yellow color under slightly acidic condition. Similarly, when bromocresol green is utilized as an indicator, acidic condition gives the indicator zone a yellow color, which is clearly distinguishable from green color under neutral or basic conditions.

Additionally, other suitable pH adjusters can include mineral acids, sulfonic acids (e.g., 2-[N-morpholino]ethane sulfonic acid ("MES"), carboxylic acids, and polymeric acids. Specific examples of suitable mineral acids are hydrochloric acid, nitric acid, phosphoric acid, and sulfuric acid. Specific examples of suitable carboxylic acids are citric acid, glycolic acid, lactic acid, acetic acid, maleic acid, gallic acid, malic acid, succinic acid, glutaric acid, benzoic acid, malonic acid, salicylic acid, gluconic acid, and mixtures thereof. Specific examples of suitable polymeric acids include straight-chain poly(acrylic) acid and its copolymers (e.g., maleic-acrylic, sulfonic-acrylic, and styrene-acrylic copolymers), cross-linked polyacrylic acids having a molecular weight of less than about 250,000, poly(methacrylic) acid, and naturally occurring polymeric acids such as carageenic acid, carboxymethyl cellulose, and alginic acid. Again, the pH adjuster results in an initial pH outside the range of typical pH for urine (either less than about 5 or greater than about 10) whereby the pH indicator is capable of a color transition when brought into contact with urine.

pH adjusters can also include bases, either inorganic bases or organic bases. Examples of such bases can include salts of carbonate such as sodium carbonate, salts of bicarbonate such as sodium bicarbonate, salts of borate such as sodium borate, salts of hydroxides such as sodium hydroxide.

pH adjusters can include buffers, either made from weak acids or weak bases. Examples of such buffers can include phosphate buffered saline and acetic buffers.

It is desired that the pH indicator be applied in a manner so that it does not substantially diffuse through the matrix of the matrix 22 (i.e., non-diffusively immobilized). This enables a user to readily detect the change in color that occurs upon reaction of the pH indicator with the urine and also prevents the pH indicator from leaching out of the matrix 22. The immobilization can be achieved by many methods such as chemical bonding, physical absorption, or using a carrier such as a polymer or a particle. In one preferred embodiment, a highly charged porous material can effectively immobilize an oppositely charged indicator. In this regard, useful charged porous substrates can include positively charged nylon membranes such as Biodyne® Plus from Pall Corporation. Porous non-woven materials such as paper tissues treated with Kymene® have also been found to be suitable charged materials to immobilize negatively charged indicators.

In certain embodiments of the present disclosure, a crosslinked network containing the pH indicator is formed on the matrix of the sensor described herein. Without intending to be limited by theory, it is believed that the crosslinked network can help durably secure the pH indicator, thereby allowing a user to more readily detect a change in its color during use. The crosslinked network can contain "intra-cross links" (i.e., covalent bonds between functional groups of a single molecule) and/or "inter-cross links" (i.e., covalent bonds between different molecules, e.g., between two pH indicator molecules or between a pH indicator molecule and the substrate surface). Crosslinking can be carried out via self crosslinking of the indicator and/or through the inclusion of a separate crosslinking agent. Suitable crosslinking agents, for instance, can include polyglycidyl ethers, such as ethylene glycol diglycidyl ether and polyethylene glycol dicglycidyl ether; acrylamides; compounds containing one or more hydrolyzable groups, such as alkoxy groups (e.g., methoxy, ethoxy and propoxy); alkoxyalkoxy groups (e.g., methoxyethoxy, ethoxyethoxy and methoxypropoxy); acyloxy groups (e.g., acetoxy and octanoyloxy); ketoxime groups (e.g., dimethylketoxime, methylketoxime and methylethylketoxime); alkenyloxy groups (e.g., vinyloxy, isopropenyloxy, and 1-ethyl-2-methylvinyloxy); amino groups (e.g., dimethylamino, diethylamino and butylamino); aminoxy groups (e.g., dimethylaminoxy and diethylaminoxy); and amide groups (e.g., N-methylacetamide and N-ethylacetamide).

Any of a variety of different crosslinking mechanisms can be employed in the present disclosure, such as thermal initiation (e.g., condensation reactions, addition reactions, etc.), electromagnetic radiation, and so forth. Some suitable examples of electromagnetic radiation that can be used in the present disclosure include, but are not limited to, electron beam radiation, natural and artificial radio isotopes (e.g., α, β, and γ rays), x-rays, neutron beams, positively-charged beams, laser beams, ultraviolet, etc. Electron beam radiation, for instance, involves the production of accelerated electrons by an electron beam device. Electron beam devices are generally well known in the art. For instance, in one embodiment, an electron beam device can be used that is available from Energy Sciences, Inc., of Woburn, Mass. under the name "Microbeam LV." Other examples of suitable electron beam devices are described in U.S. Pat. No. 5,003,178 to Livesay; U.S. Pat. No. 5,962,995 to Avnery; U.S. Pat. No. 6,407,492 to Avnery, et al., which are incorporated herein in their entirety by reference thereto for all purposes. The wavelength X of the radiation can vary for different types of radiation of the electromagnetic radiation spectrum, such as from about $10^{-14}$ meters to about $10^{-5}$ meters. Electron beam radiation, for instance, has a wavelength λ of from about $10^{-13}$ meters to about $10^{-9}$ meters. Besides selecting the particular wavelength λ of the electromagnetic radiation, other parameters can also be selected to control the degree of crosslinking. For example, the dosage can range from about 0.1 megarads (Mrads) to about 10 Mrads, and in some embodiments, from about 1 Mrads to about 5 Mrads.

The source of electromagnetic radiation can be any radiation source known to those of ordinary skill in the art. For example, an excimer lamp or a mercury lamp with a D-bulb can be used. Other specialty-doped lamps that emit radiation at a fairly narrow emission peak can be used with photoinitiators which have an equivalent absorption maximum. For example, the V-bulb, available from Fusion Systems, is another suitable lamp for use. In addition, specialty lamps having a specific emission band can be manufactured for use with one or more specific photoinitiators.

Initiators can be employed in some embodiments that enhance the functionality of the selected crosslinking technique. Thermal initiators, for instance, can be employed in certain embodiments, such as azo, peroxide, persulfate, and redox initiators. Representative examples of suitable thermal initiators include azo initiators such as 2,2'-azobis(2,4-dimethylvaleronitrile), 2,2'-azobis(isobutyronitrile), 2,2'-azobis-2-methylbutyronitrile, 1,1'-azobis(1-cyclohexanecarbonitrile), 2,2'-azobis(methyl isobutyrate), 2,2'-azobis(2-amidinopropane)dihydrochloride, and 2,2'-azobis(4-methoxy-2,4-dimethylvaleronitrile); peroxide initiators such as benzoyl peroxide, acetyl peroxide, lauroyl peroxide, decanoyl peroxide, dicetyl peroxydicarbonate, di(4-t-butylcyclohexyl)peroxydicarbonate, di(2-ethylhexyl)peroxydicarbonate, t-butylperoxypivalate, t-butylperoxy-2-ethylhexanoate, and dicumyl peroxide; persulfate initiators such as potassium persulfate, sodium persulfate, and ammonium persulfate; redox (oxidation-reduction) initiators such as combinations of the above persulfate initiators with reducing agents such as sodium metabisulfite and sodium bisulfite, systems based on organic peroxides and tertiary amines, and systems based on organic hydroperoxides and transition metals; other initiators such as pinacols; and the like (and mixtures thereof). Azo compounds and peroxides are generally preferred. Photoinitiators can likewise be employed, such as substituted acetophenones, such as benzyl dimethyl ketal and 1-hydroxycyclohexyl phenyl ketone; substituted alpha-ketols, such as 2-methyl-2-hydroxypropiophenone; benzoin ethers, such as benzoin methyl ether and benzoin isopropyl ether; substituted benzoin ethers, such as anisoin methyl ether; aromatic sulfonyl chlorides; photoactive oximes; and so forth (and mixtures thereof). Other suitable photoinitiators can be described in U.S. Pat. No. 6,486,227 to Nohr, et al. and U.S. Pat. No. 6,780,896 to MacDonald, et al., both of which are incorporated herein by reference.

Although not required, additional components can also be employed within the crosslinked network to facilitate the securement of the pH indicator. For example, an anchoring compound can be employed that links the pH indicator to the surface of matrix and further improves the durability of the pH indicator on the sensor. Typically, the anchoring compound is larger in size than the pH indicator, which improves its likelihood of remaining on the surface of the chromatographic medium during use. For example, the anchoring compound can include a macromolecular compound, such as a polymer, oligomer, dendrimer, particle, etc. Polymeric anchoring compounds can be natural, synthetic, or combinations thereof. Examples of natural polymeric anchoring compounds include, for instance, polypeptides, proteins, DNA/RNA and polysaccharides (e.g., glucose-based polymers). Examples of synthetic polymeric anchoring compounds include, for instance, polyacrylic acid and polyvinyl alcohols. One particular example of a polysaccharide anchoring compound is activated dextran. In some embodiments, the anchoring compound can be a particle (sometimes referred to as a "bead" or "microbead"). Naturally occurring particles, such as nuclei, mycoplasma, plasmids, plastids, mammalian cells (e.g., erythrocyte ghosts), unicellular microorganisms (e.g., bacteria), polysaccharides (e.g., agarose), etc., can be used. Further, synthetic particles can also be utilized. For example, in one embodiment, latex microparticles are utilized. Although any synthetic particle can be used, the particles are typically formed from polystyrene, butadiene styrenes, styreneacrylic-vinyl terpolymer, polymethylmethacrylate, polyethylmethacrylate, styrene-maleic anhydride copolymer, polyvinyl acetate, polyvinylpyridine, polydivinylbenzene, polybutyleneterephthalate, acrylonitrile, vinylchloride-acrylates, and so forth, or an aldehyde, carboxyl, amino, hydroxyl, or hydrazide derivative thereof. When utilized, the shape of the particles can generally vary. In one particular embodiment, for instance, the particles are spherical in shape. However, it should be understood that other shapes are also contemplated such as plates, rods, discs, bars, tubes, irregular shapes, etc. In addition, the size of the particles can also vary. For instance, the average size (e.g., diameter) of the particles can range from about 0.1 nanometers to about 1,000 microns, in some embodiments, from about 0.1 nanometers to about 100 microns, and in some embodiments, from about 1 nanometer to about 10 microns.

The manner in which the anchoring compound is used to link the pH indicator and the matrix can vary. In one embodiment, for instance, the anchoring compound is attached to the pH indicator prior to application of both to the matrix. In other embodiments, the anchoring compound can be bonded to the matrix prior to application of the pH indicator. In still other embodiments, the materials can be applied as separate components to the matrix and attachment reactions can take place in situ, optionally at the same time as the crosslinking of the network. For instance, the pH indicator can bind the anchoring compound, the anchoring compound can bind the matrix, and simultaneously, cross-linking reactions can take place between anchoring compounds, between indicators, or between the two. In one such embodiment, the cross-linked network thus formed can be physically held on the matrix without the need for bonding between the matrix and the other components of the system. In particular, the crosslinked network, portions of which can extend within and among the pores of the matrix, can be physically constrained on the matrix, even without specific bonds forming between the matrix and the components of the crosslinked network.

In the case of bonds being formed between the sensor components, attachment of the anchoring compound to a matrix as well as attachment of the anchoring compound to the pH indicator can be accomplished using carboxylic, amino, aldehyde, bromoacetyl, iodoacetyl, thiol, epoxy or other reactive functional groups, as well as residual free radicals and radical cations, through which a binding reaction can be accomplished and according to any suitable methods, e.g., thermal processes, photo-initiated processes, catalyzed reactions, and the like. For example, a matrix can be amine-functionalized through contact with an amine-containing compound, such as 3-aminopropyltriethoxy silane, to increase the amine functionality of the surface and bind the anchoring compound to the surface via, e.g., aldehyde functionality of the anchoring compound. A surface functional group can also be incorporated on a particle-type anchoring compound as a reactive functionality, for instance when the surface of the particle contains a relatively high surface concentration of polar groups. In certain cases, the particle can be capable of direct bonding to matrix and/or a pH indicator without the need for further modification.

It should be understood that, besides covalent bonding, other attachment techniques, such as charge-charge interactions, can also be utilized for attaching the anchoring compound to the chromatographic medium and/or for attaching the pH indicator to the anchoring compound. For instance, a charged anchoring compound, such as a positively charged polyelectrolyte anchoring compound, can be immobilized on a negatively charged matrix, such as negatively charged porous nitrocellulose membrane, through charge-charge interactions between the two. Similarly, a negatively charged indicator, such as a diazonium ion, can be immobilized on a positively charged anchoring compound.

In the illustrated embodiment, the matrix 22 also defines a thermochromic zone 28. To facilitate detection of urine, a mixture of a thermochromic material and a temperature change agent can be disposed in the thermochromic zone. The temperature change agent, when brought into contact with urine, is capable of causing a temperature change in the thermochromic material which results in a color transition.

In this regard, thermochromic materials can include thermochromic liquid crystalline materials, thermochromic inks, thermochromic dyes, and combinations thereof. The thermochromic inks described herein are intended to serve as temperature indication mechanisms. As used herein "thermochromic" refers to materials that change their reflected color as a function of temperature. Thermochromic dyes that can change color are typically called leuco dyes. Suitable thermochromic inks are commercially available from Polytex D'Pere. Additional suitable thermochromic inks are detailed in U.S. Pat. Nos. 4,121,011, 4,826,550, 5,389,093, and 5,221,228. The thermochromic materials used can be in the form of fine pigments particles, microencapsulated materials, molecular materials and the like.

The thermochromic material described herein can change color as a result of either heating or cooling. The temperatures causing such color changes can vary depending on the particular thermochromic material selected.

As described above, the thermochromic material is combined with a temperature change agent, such as a cooling or warming agent, depending upon the type of thermochromic material selected.

A variety of cooling agents can be employed. For example, useful cooling agents can include menthol, xylitol, sorbitol, erythritol, menthane, menthone, ketals, menthone ketals, menthone glycerol ketals, substituted p-menthanes, acyclic carboxamides, mono menthyl glutarate, substituted cyclohexanamides, substituted cyclohexane carboxamides, substituted ureas and sulfonamides, substituted menthanols, hydroxymethyl and hydroxymethyl derivatives of p-menthane, 2-mercapto-cyclo-decanone, 2-isopropanyl-5-methyl-cyclohexanol, hydroxycarboxylic acids with 2-6 carbon atoms, cyclohexanamides, menthyl acetate, isopulegol, menthyl lactate, menthyl salicylate, N,2,3-trimethyl-2-isopropyl butanamide (WS-23), N-ethyl-p-menthane-3-carboxamide (WS-3), menthyl succinate, 3,1-menthoxypropane 1,2-diol, p-menthane-3,8-diols, and glutarate esters, among others. These and other suitable cooling agents are further described in the following U.S. patents, all of which are incorporated in their entirety by reference hereto: U.S. Pat. Nos. 4,230,688; 4032,661; 4,459,425; 4,136,163; 5,266,592; 6,627,233. Such cooling agents can cause a temperature decrease when brought into contact with urine.

Similarly, a variety of warming agents can be utilized in connection with the present disclosure. Warming agents can include vanillyl alcohol n-butylether (TK-1000) supplied by Takasago Perfumary Company Limited, Tokyo, Japan, vanillyl alcohol n-propylether, vanillyl alcohol isopropylether, vanillyl alcohol isobutylether, vanillyl alcohol n-aminoether, vanillyl alcohol isoamyleather, vanillyl alcohol n-hexyleather, vanillyl alcohol methylether, vanillyl alcohol ethyleather, gingerol, shogaol, paradol, zingerone, capsaicin, dihydrocapsaicin, nordihydrocapsaicin, homocapsaicin, homodilhydrocapsaicin, ethanol, isopropyl alcohol, iso-amylalcohol, benzyl alcohol, glycerine, and combinations thereof. Such warming agents can cause a temperature increase when brought into contact with urine.

It should be understood that any suitable amount of cooling or warming agent can be utilized so as to cause a temperature change in the thermochromic material which results in a color transition. For instance, in certain embodiments, the cooling or warming agent can be present in an amount ranging from about 1 to about 99 weight percent of the thermochromic mixture, in particular from about 15 to about 30 weight percent. In certain embodiments, the thermochromic material can be present in an amount ranging from about 99 to about 1 weight percent of the thermochromic mixture.

The thermochromic mixture can be applied to the matrix in any suitable manner and can be applied so as to form letters, words, graphics symbols, icons, trademarks, instructions and the like.

In certain embodiments, sensors made in accordance with the present disclosure are able to maintain signal strength for at least about 10 minutes, more particularly at least about 30 minutes, more particularly at least about 1 hour. Additionally, such sensors can be subjected to multiple urine insults and still produce accurate test results.

One particular embodiment of a method for detecting the presence of absence of urine using the sensor 20 of FIG. 1 will now be described in more detail. Initially, a urine test sample is applied to the matrix 22. The urine sample contacts the pH indicator zone 26 where the change in pH is detected by a pH indicator, which is capable of a color transition when brought into contact with urine. Similarly, the pH indicator contacts the thermochromic zone 28 causing the temperature change agent to change the temperature of the thermochromic ink, resulting in a color transition.

The present disclosure provides a relatively simple, compact and cost-efficient sensor for accurately detecting the presence or absence of urine. The test result can be visible so that it is readily observed by the person performing the test in a prompt manner and under test conditions conducive to highly reliable and consistent test results.

In accordance with the present disclosure, one or more sensors described herein can also be integrated into an absorbent article. An "absorbent article" generally refers to any article capable of absorbing water or other fluids. Examples of some absorbent articles include, but are not limited to, personal care absorbent articles, such as diapers, training pants, absorbent underpants, incontinence articles, feminine hygiene products (e.g., sanitary napkins), swim wear, baby wipes, and so forth; medical absorbent articles, such as garments, fenestration materials, underzones, bedzones, bandages, absorbent drapes, and medical wipes; food service wipers; clothing articles; and so forth. Materials and processes suitable for forming such absorbent articles are well known to those skilled in the art. Typically, absorbent articles include a substantially liquid-impermeable layer (e.g., outer cover), a liquid-permeable layer (e.g., bodyside liner, surge layer, etc.), and an absorbent core.

Figure 2:
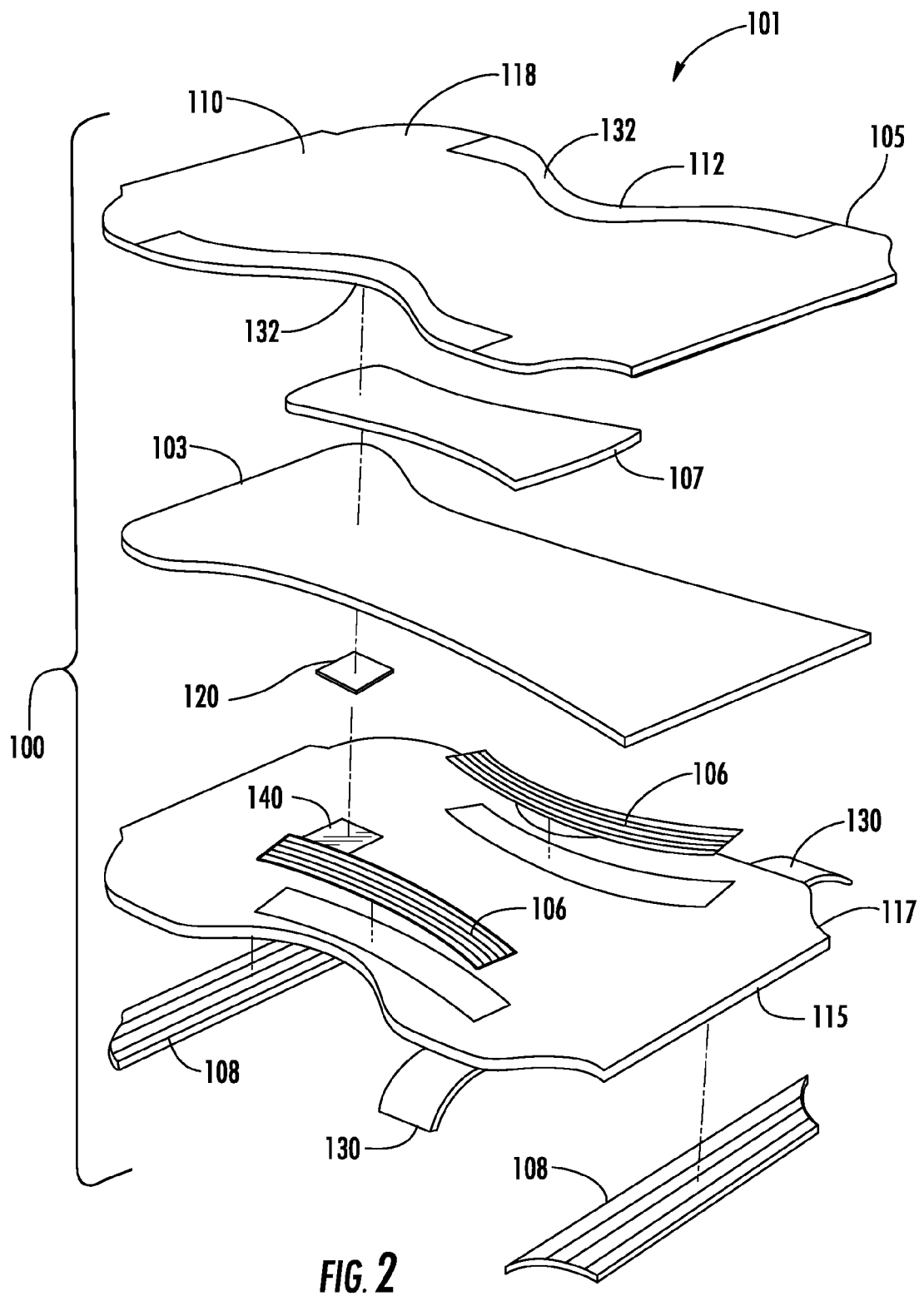
FIG. 2 is a perspective view of one embodiment of a sensor that can be used in the present disclosure.

Various embodiments of an absorbent article that can be formed according to the present disclosure will now be described in more detail. For purposes of illustration only, an absorbent article is shown in FIG. 2 as a diaper 101. In the illustrated embodiment, the diaper 101 is shown as having an hourglass shape in an unfastened configuration. However, other shapes can of course be utilized, such as a generally rectangular shape, T-shape, or I-shape. As shown, the diaper 101 includes a chassis formed by various components, including an outer cover 117, bodyside liner 105, absorbent core 103, and surge layer 107. It should be understood, however, that other layers can also be used in exemplary embodiments of the present disclosure. Likewise, one or more of the layers referred to in FIG. 2 can also be eliminated in certain exemplary embodiments of the present disclosure.

The bodyside liner 105 is generally employed to help isolate the wearer's skin from liquids held in the absorbent core 103. For example, the liner 105 presents a bodyfacing surface that is typically compliant, soft feeling, and non-irritating to the wearer's skin. Typically, the liner 105 is also less hydrophilic than the absorbent core 103 so that its surface remains relatively dry to the wearer. As indicated above, the liner 105 can be liquid-permeable to permit liquid to readily penetrate through its thickness. Exemplary liner constructions that contain a nonwoven web are described in U.S. Pat. No. 5,192,606 to Proxmire, et al.; U.S. Pat. No. 5,702,377 to Collier, IV, et al.; U.S. Pat. No. 5,931,823 to Stokes, et al.; U.S. Pat. No. 6,060,638 to Paul et al.; and U.S. Pat. No. 6,150,002 to Varona, as well as U.S. Patent Application Publication Nos. 2004/0102750 to Jameson; 2005/0054255 to Morman, et al.; and 2005/0059941 to Baldwin, et al., all of which are incorporated herein in their entirety by reference thereto for all purposes.

The diaper 101 can also include a surge layer 107 that helps to decelerate and diffuse surges or gushes of liquid that can be rapidly introduced into the absorbent core 103. Desirably, the surge layer 107 rapidly accepts and temporarily holds the liquid prior to releasing it into the storage or retention portions of the absorbent core 103. In the illustrated embodiment, for example, the surge layer 107 is interposed between an inwardly facing surface 116 of the bodyside liner 105 and the absorbent core 103. Alternatively, the surge layer 107 can be located on an outwardly facing surface 118 of the bodyside liner 105. The surge layer 107 is typically constructed from highly liquid-permeable materials. Examples of suitable surge layers are described in U.S. Pat. No. 5,486,166 to Ellis, et al. and U.S. Pat. No. 5,490,846 to Ellis, et al., which are incorporated herein in their entirety by reference thereto for all purposes.

The outer cover 117 is typically formed from a material that is substantially impermeable to liquids. For example, the outer cover 117 can be formed from a thin plastic film or other flexible liquid-impermeable material. In one embodiment, the outer cover 117 is formed from a polyethylene film having a thickness of from about 0.01 millimeter to about 0.05 millimeter. The film can be impermeable to liquids, but permeable to gases and water vapor (i.e., "breathable"). This permits vapors to escape from the absorbent core 103, but still prevents liquid exudates from passing through the outer cover 117. If a more cloth-like feeling is desired, the outer cover 117 can be formed from a polyolefin film laminated to a nonwoven web. For example, a stretch-thinned polypropylene film can be thermally laminated to a spunbond web of polypropylene fibers.

Besides the above-mentioned components, the diaper 101 can also contain various other components as is known in the art. For example, the diaper 101 can also contain a substantially hydrophilic tissue wrapsheet (not illustrated) that helps maintain the integrity of the fibrous structure of the absorbent core 103. The tissue wrapsheet is typically placed about the absorbent core 103 over at least the two major facing surfaces thereof, and composed of an absorbent cellulosic material, such as creped wadding or a high wet-strength tissue. The tissue wrapsheet can be configured to provide a wicking layer that helps to rapidly distribute liquid over the mass of absorbent fibers of the absorbent core 103. The wrapsheet material on one side of the absorbent fibrous mass can be bonded to the wrapsheet located on the opposite side of the fibrous mass to effectively entrap the absorbent core 103. Furthermore, the diaper 101 can also include a ventilation layer (not shown) that is positioned between the absorbent core 103 and the outer cover 117. When utilized, the ventilation layer can help insulate the outer cover 117 from the absorbent core 103, thereby reducing dampness in the outer cover 117. Examples of such ventilation layers can include a nonwoven web laminated to a breathable film, such as described in U.S. Pat. No. 6,663,611 to Blaney, et al., which is incorporated herein in its entirety by reference thereto for all purposes.

In some embodiments, the diaper 101 can also include a pair of side panels (or ears) (not shown) that extend from the side edges 132 of the diaper 101 into one of the waist regions. The side panels can be integrally formed with a selected diaper component. For example, the side panels can be integrally formed with the outer cover 117 or from the material employed to provide the top surface. In alternative configurations, the side panels can be provided by members connected and assembled to the outer cover 117, the top surface, between the outer cover 117 and top surface, or in various other configurations. If desired, the side panels can be elasticized or otherwise rendered elastomeric by use of the elastic nonwoven composite of the present disclosure. Examples of absorbent articles that include elasticized side panels and selectively configured fastener tabs are described in PCT Patent Application WO 95/16425 to Roessler; U.S. Pat. No. 5,399,219 to Roessler et al.; U.S. Pat. No. 5,540,796 to Fries;

and U.S. Pat. No. 5,595,618 to Fries, each of which is incorporated herein in its entirety by reference thereto for all purposes.

As representatively illustrated in FIG. 2, the diaper 101 can also include a pair of containment flaps 112 that are configured to provide a barrier and to contain the lateral flow of body exudates. The containment flaps 112 can be located along the laterally opposed side edges 132 of the bodyside liner 105 adjacent the side edges of the absorbent core 103. The containment flaps 112 can extend longitudinally along the entire length of the absorbent core 103, or can only extend partially along the length of the absorbent core 103. When the containment flaps 112 are shorter in length than the absorbent core 103, they can be selectively positioned anywhere along the side edges 132 of diaper 101 in a crotch region 110. In one embodiment, the containment flaps 112 extend along the entire length of the absorbent core 103 to better contain the body exudates. Such containment flaps 112 are generally well known to those skilled in the art. For example, suitable constructions and arrangements for the containment flaps 112 are described in U.S. Pat. No. 4,704,116 to Enloe, which is incorporated herein in its entirety by reference thereto for all purposes.

To provide improved fit and to help reduce leakage of body exudates, the diaper 101 can be elasticized with suitable elastic members, as further explained below. For example, as representatively illustrated in FIG. 2, the diaper 101 can include leg elastics 106 constructed to operably tension the side margins of the diaper 101 to provide elasticized leg bands which can closely fit around the legs of the wearer to reduce leakage and provide improved comfort and appearance. Waist elastics 108 can also be employed to elasticize the end margins of the diaper 101 to provide elasticized waistbands. The waist elastics 108 are configured to provide a resilient, comfortably close fit around the waist of the wearer.

The diaper 101 can also include one or more fasteners 130. For example, two flexible fasteners 130 are illustrated in FIG. 2 on opposite side edges of waist regions to create a waist opening and a pair of leg openings about the wearer. The shape of the fasteners 130 can generally vary, but can include, for instance, generally rectangular shapes, square shapes, circular shapes, triangular shapes, oval shapes, linear shapes, and so forth. The fasteners can include, for instance, a hook-and-loop material, buttons, pins, snaps, adhesive tape fasteners, cohesives, fabric-and-loop fasteners, etc. In one particular embodiment, each fastener 130 includes a separate piece of hook material affixed to the inside surface of a flexible backing.

The various regions and/or components of the diaper 101 can be assembled together using any known attachment mechanism, such as adhesive, ultrasonic, thermal bonds, etc. Suitable adhesives can include, for instance, hot melt adhesives, pressure-sensitive adhesives, and so forth. When utilized, the adhesive can be applied as a uniform layer, a patterned layer, a sprayed pattern, or any of separate lines, swirls or dots. In the illustrated embodiment, for example, the outer cover 117 and bodyside liner 105 are assembled to each other and to the absorbent core 103 using an adhesive. Alternatively, the absorbent core 103 can be connected to the outer cover 117 using conventional fasteners, such as buttons, hook and loop type fasteners, adhesive tape fasteners, and so forth. Similarly, other diaper components, such as the leg elastic members 106, waist elastic members 108 and fasteners 130, can also be assembled into the diaper 101 using any attachment mechanism.

Generally speaking, the sensors of the present disclosure can be incorporated into the absorbent article in a variety of different orientations and configurations, so long as the sensor is capable of receiving urine and providing a signal to a user or caregiver regarding the presence or absence of urine. For example, sensor can be visible to the user or caregiver so that a simple, accurate, and rapid indication of wetness can be provided. The visibility can be accomplished in a variety of ways. For example, in some embodiments, the absorbent article can include a transparent or transluscent portion 140 (e.g., window, film, etc.) that allows the sensor to be readily viewed without removal of the absorbent article from the wearer and/or without disassembly of the absorbent article. In other embodiments, the sensor can extend through a hole or aperture in the absorbent article for observation. In still other embodiments, the sensor can simply be positioned on a surface of the absorbent article for observation.

Regardless of the particular manner in which it is integrated, urine can be directly discharged to a portion of the sensor, a liquid permeable cover or other material surrounding sensor, or can be discharged onto a component of the absorbent article into which the sensor 120 has been integrated.

The present disclosure can be better understood with reference to the following examples.

EXAMPLES

1. Preparation and Testing of the Sensor:

0.5 mg/ml of bromochlorophenol blue and 5 mg/ml oxalic acid in water were prepared. 10 ml of the solution was placed in a Petri dish. A 10 cm×10 cm piece of Biodyne® Plus membrane from Pall Co. was loaded in the Petri dish and soaked in the solution. The membrane was soaked for 10 minutes and it was then dried at 45° C. for 2 hours. The membrane was cut into pieces measuring 5 cm×1 cm. The color of the sensor was yellow when dry. The color changed to deep blue once in contact with urine.

2. Preparation and Testing of the Sensor:

0.2 mg/ml of bromocresol green and 2 mg/ml citric acid in water were prepared. 10 ml of the solution was placed in a Petri dish. A 10 cm×10 cm piece of Biodyne® Plus membrane from Pall Co. was loaded in the Petri dish and soaked in the solution. The membrane was soaked for 10 minutes and it was then air-dried at room temperature. The membrane was cut into pieces measuring 5 cm×1 cm. The color of the sensor was yellow when dry. The color changed to green once in contact with urine.

3. Absorbant Article with the Sensor:

A rectangular hole around the center of the outer cover of a Huggies diaper was made by removing the portion of the outer cover. The sensors prepared in above examples were then inserted against the absorbant core. A transparent Scotch tape was used to cover, secure and sandwich the sensors. 5 ml of urine was applied from the center of the inner side. The sensor changes color from yellow to blue (using bromophenol blue) or green (using bromocresol green).

4. Preparation and Testing of the Sensor:

Filter paper from Waterman was soaked with 0.5% Kymene from Hercules and heated at 70° C. for 2 hours. The filter paper was then soaked with 0.5 mg/ml bromocresol green with 2 mg/ml citric acid in ethanol for 5 minutes. The filter paper was then dried at room temperature. The paper was cut into pieces measuring 5 cm×1 cm. The color of the sensor was yellow when dry. The color changed to green once in contact with urine.

5. Preparation and Testing of the Sensor:

Filter paper from Waterman was soaked with 0.5% Kymene from Hercules and heated at 70° C. for 2 hours. 1 mg/ml bromocresol green with 5 mg/ml citric acid in ethanol was sprayed on the filter paper. The filter paper was then dried at room temperature. The paper was cut into pieces measuring 5 cm×1 cm. The color of the sensor was yellow when dry. The color changed to green once in contact with urine.

6. Leaching Test 20 cm×20 cm sensors prepared using above procedures were cut into pieces of 1 cm×1 cm and put into a 20 ml of water solution with 100 mg/ml NaCl for two days. The sensors were then removed and the indicator concentrations were measured by spectrophotometer. For the sensors using Biodyne Plus membrane, no measurable dye was leached into the solution. For the sensors using Kymene-treated filter paper, less than 6% dye was leached out.

7. Xylitol was added to Polytex D'Pere thermochromic ink. Upon initial addition of the xylitol to the ink, the color was very vibrant. The mixed ink solution was then spread onto XP-8635Y film and allowed to dry. The ink greatly decreased in color and visibility upon drying. When the film was exposed to liquid, the ink became highly vibrant again and stayed highly visible for several minutes, in some cases up to an hour or more.

In the interests of brevity and conciseness, any ranges of values set forth in this specification are to be construed as written description support for claims reciting any sub-ranges having endpoints which are whole number values within the specified range in question. By way of a hypothetical illustrative example, a disclosure in this specification of a range of 1-5 shall be considered to support claims to any of the following sub-ranges: 1-4; 1-3; 1-2; 2-5; 2-4; 2-3; 3-5; 3-4; and 4-5.

These and other modifications and variations to the present disclosure can be practiced by those of ordinary skill in the art, without departing from the spirit and scope of the present disclosure, which is more particularly set forth in the appended claims. In addition, it should be understood that aspects of the various embodiments can be interchanged both in whole or in part. Furthermore, those of ordinary skill in the art will appreciate that the foregoing description is by way of example only, and is not intended to limit the disclosure so further described in such appended claims.

What is claimed is:

1. A method for detecting the presence of urine, the method comprising:
   providing a urine indicating sensor comprising a matrix, the matrix having a mixture of a thermochromic material and a temperature change agent disposed thereon, the temperature change agent configured to cause either a temperature increase or a temperature decrease when brought into contact with urine so as to be capable of causing a temperature change in the thermochromic material resulting in a color transition, wherein the temperature change member comprises xylitol, sorbitol, or combinations thereof;
   contacting urine with the matrix of the sensor; and
   determining the presence of urine based on whether the thermochromic material undergoes a color transition.

2. The method of claim 1, wherein the thermochromic material comprises thermochromic liquid crystalline material, thermochromic ink, thermochromic dye, or combinations thereof.

3. The method of claim 1, wherein the temperature change agent comprises a polyol.

4. The method of claim 1, further comprising:
   allowing a period of time to pass wherein the thermochromic material color reverts back to its original color;
   contacting urine with the matrix of the sensor; and
   determining the presence of urine based on whether the thermochromic material undergoes a color transition.

5. The method of claim 1, wherein the matrix further has a pH indicator non-diffusively immobilized thereon, the pH indicator being capable of a color transition when in contact with urine, and wherein the presence of urine is also determined based on whether the pH indicator undergoes a color transition.

6. A sensor for determining the presence of absence of urine, the sensor comprising a matrix defining:
   a thermochromic zone having a mixture of a thermochromic material and a temperature change agent disposed therein, the temperature change agent configured to cause either a temperature increase or a temperature decrease when brought into contact with urine so as to be capable of causing a temperature change in the thermochromic material resulting in a color transition, wherein the temperature change member comprises xylitol, sorbitol, or combinations thereof.

7. The sensor of claim 6, further comprising a pH indicator zone having a pH indicator non-diffusively immobilized therein, the pH indicator being capable of a color transition when in contact with urine.

8. The sensor of claim 7, wherein the pH indicator zone further comprises a pH adjuster, the pH adjuster comprising an acid, base, buffer, or combination thereof.

9. The sensor of claim 7, wherein the pH indicator comprises Chlorobromophenol blue, Bromophenol blue, Bromocresol blue, methyl violet, methyl orange, Congo red, leucomalachite green, methyl yellow, brornophenol blue, malachite green, brillian green, crystal violet, erythrosin B, methyl green, methyl violet 2B, picric acid, napthol yellow S, quinaldine red, basic fuchsin, nile blue A, thymolphthalein, aniline blue W.S., alizarin yellow GG, morgant orange I, tropaeolin O, orange G, acid fuchsin, thiazol yellow G, indigo carmine, phenolphthalein, thymolphthalein, alizarine yellow R, or derivatives or combinations thereof.

10. The sensor of claim 7, wherein the matrix is a charged porous matrix capable of a charge-charge interaction with the pH indicator.

11. The sensor of claim 7, wherein the pH indicator is capable of a color transition when exposed to a pH of less than about 10 and greater than about 5.

12. The sensor of claim 6, wherein the thermochromic material comprises thermochromic liquid crystalline material, thermochromic ink, thermochromic dye, or combinations thereof.

13. An absorbent article capable of determining the determining the presence of absence of urine:
   a substantially liquid impermeable layer;
   a liquid permeable layer;
   an absorbent core positioned between the substantially liquid impermeable layer and the liquid permeable layer; and
   a sensor integrated into the article and positioned such that the sensor is in fluid communication with the urine when provided by a wearer of the article, the sensor comprising a matrix defining:
   a thermochromic zone having a mixture of a thermochromic material and a temperature change agent disposed therein, the temperature change agent configured to cause either a temperature increase or a temperature decrease when brought into contact with urine so as to be capable of causing a temperature change in the thermochromic material resulting in a color transition, wherein the temperature change member comprises xylitol, sorbitol, or combinations thereof.

14. The absorbent article of claim 13, wherein the matrix further comprises a pH indicator zone having a pH indicator non-diffusively immobilized therein, the pH indicator being capable of a color transition when in contact with urine.

15. The absorbent article of claim 14, wherein the pH indicator comprises Chlorobromophenol blue, Bromophenol blue, Bromocresol blue, methyl violet, methyl orange, Congo red, leucomalachite green, methyl yellow, bromophenol blue, malachite green, brillian green, crystal violet, erythrosin B, methyl green, methyl violet 2B, picric acid, napthol yellow S, quinaldine red, basic fuchsin, nile blue A, thymolphthalein, aniline blue W.S., alizarin yellow GG, morgant orange I, tropaeolin O, orange G, acid fuchsin, thiazol yellow G, indigo carmine, phenolphthalein, thymolphthalein, alizarine yellow R, or derivatives or combinations thereof.

16. The absorbent article of claim 13, wherein the thermochromic material comprises thermochromic liquid crystalline material, thermochromic ink, thermochromic dye, or combinations thereof.

17. The absorbent article of claim 13, wherein the absorbent article defines a window through which the sensor is observable.

* * * * *

UNITED STATES PATENT AND TRADEMARK OFFICE
CERTIFICATE OF CORRECTION

PATENT NO. : 8,134,042 B2
APPLICATION NO. : 11/956657
DATED : March 13, 2012
INVENTOR(S) : Song et al.

Page 1 of 1

It is certified that error appears in the above-identified patent and that said Letters Patent is hereby corrected as shown below:

In the Claims

Claim 6, line 1 - after the word "presence" please delete "of" and insert --or--

Claim 9, line 5 - after the words "malachite green," please delete "billian" and insert --brilliant--

Claim 13, line 1 - after the words "capable of" please delete the first instance of "determining the"

Claim 13, line 2 - after the word "presence" please delete "of" and insert --or--

Claim 15, line 5 - after the words "leucomalachite green," please delete "billian" and insert --brilliant--

Signed and Sealed this
Seventh Day of January, 2014

Margaret A. Focarino
*Commissioner for Patents of the United States Patent and Trademark Office*